(12) United States Patent
Khulusi

(10) Patent No.: US 7,096,514 B2
(45) Date of Patent: Aug. 29, 2006

(54) PROTECTIVE GOGGLES

(76) Inventor: Basimah Khulusi, 930 Broadway, Suite 401, Kansas City, MO (US) 64105

(*) Notice: Subject to any disclaimer, the term of this patent is extended or adjusted under 35 U.S.C. 154(b) by 315 days.

(21) Appl. No.: 10/691,189

(22) Filed: Oct. 22, 2003

(65) Prior Publication Data

US 2004/0078875 A1  Apr. 29, 2004

Related U.S. Application Data

(60) Provisional application No. 60/420,822, filed on Oct. 24, 2002.

(51) Int. Cl.
*A61F 9/02* (2006.01)

(52) U.S. Cl. ............................................. 2/430; 2/436

(58) Field of Classification Search .................. 2/9, 2/12, 15, 427, 436, 439, 441, 444, 447, 449, 2/430; 351/41, 44, 162, 159
See application file for complete search history.

(56) References Cited

U.S. PATENT DOCUMENTS

| 2,422,534 | A | * | 6/1947 | Du Bois | 2/441 |
| 3,031,674 | A | * | 5/1962 | Ring | 2/441 |
| 3,924,271 | A | * | 12/1975 | Hirschmann, Jr. | 2/439 |
| 4,850,058 | A | * | 7/1989 | Cheng | 2/439 |
| 5,138,723 | A | * | 8/1992 | Bolle | 2/430 |
| 2003/0033661 | A1 | * | 2/2003 | Huh | 2/436 |

* cited by examiner

*Primary Examiner*—Katherine M. Moran
(74) *Attorney, Agent, or Firm*—Lathrop & Gage LC

(57) ABSTRACT

A goggle having features of the present invention comprises a transparent housing with an arcuate upper surface with a first end and a second end, a planar frontal surface, a centrally disposed nose bridge and a first and second lower panel disposed opposite the nose bridge. The first and second lower panel join the arcuate upper surface proximate the arcuate upper surface first end and second end while the housing is contoured to conform to the topography of the wearer's face. Vents are disposed adjacent the nose bridge and means for supporting the goggle on the head of the wearer.

9 Claims, 14 Drawing Sheets

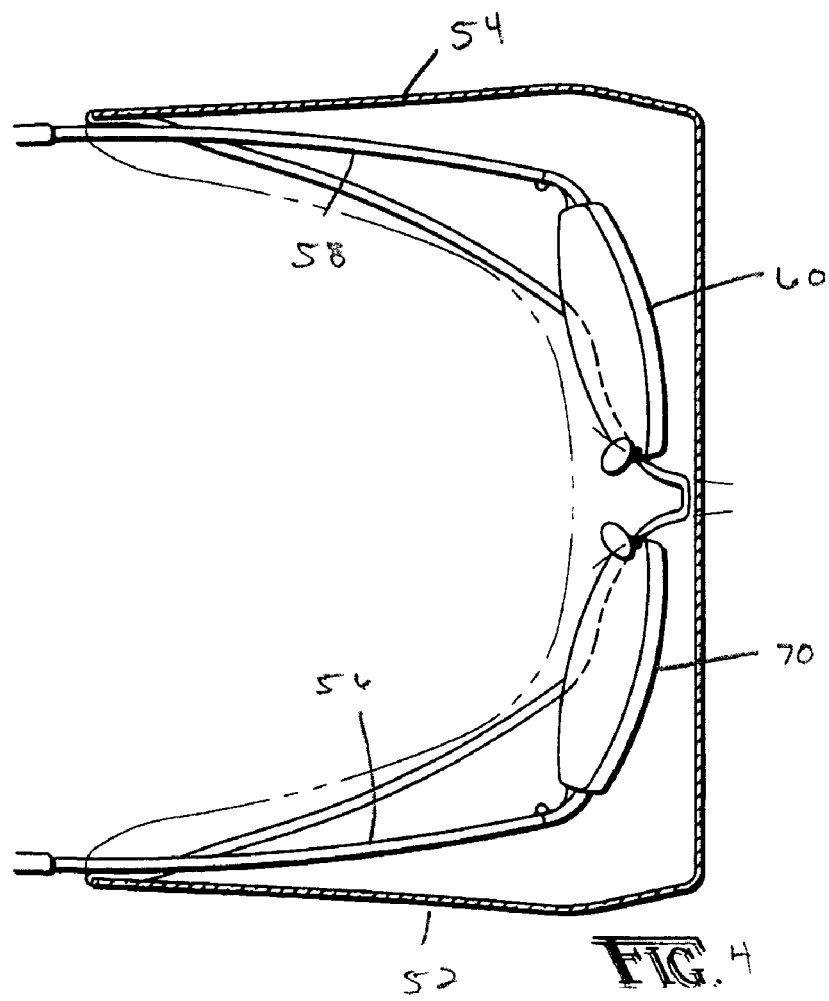
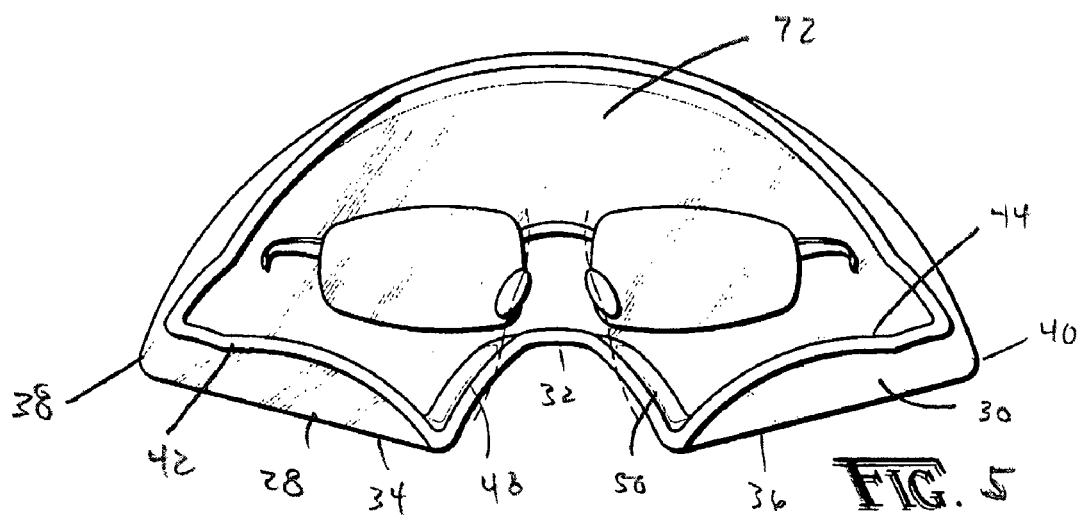

PROTECTIVE GOGGLES

RELATED APPLICATION

This application claims priority and is the nonprovisional application of U.S. Patent Application Ser. No. 60/420,822, filed Oct. 24, 2002, which is incorporated herein by reference.

FIELD OF THE INVENTION

This invention relates generally to personal safety equipment and in particular to safety goggles suitable for industrial and sporting use and to goggles that can be easily manufactured and assembled.

DESCRIPTION OF THE RELATED ART

Virtually all industrial and sports injuries to the eye are avoidable if suitable eye protection such as goggles are provided. Eye trauma is the leading cause of blindness worldwide. It is estimated that each day two thousand individuals in the United States suffer eye injuries on the job or while playing sports. These injuries incur more than $924 million annually in worker's compensation, and nearly $4 billion in wage and productivity losses according to the U.S. Bureau of Labor Statistics. Nearly 90 percent of all workplace and sports related injuries are preventable with the proper eyewear and safety measures according to statistics from the organization Prevent Blindness America.

It is evident from the eye injury statistics that large numbers of individuals are not wearing eye protection while in the vicinity of activities that present dangers to the eye. Also, injuries are still occurring despite the use of protective eyewear. Those individuals being injured often wear inappropriate or ill-fitting eyewear for the task being undertaken or do not wear protective eyewear at all times while undertaking the task. The literature suggests that the main reasons individuals do not wear protective eyewear relate to issues of comfort, style, restricted vision, and safety equipment not provided by employers.

OSHA standards require that employers provide, and workers wear, suitable eye protection. To be effective, the eyewear must be the appropriate type and properly fitted. For example, the Bureau of Labor Statistics survey revealed that 94 percent of injuries to workers wearing eye protection resulted from objects or caustics going around or under the protector. But less than six percent of the injuries happened to workers wearing goggles, which generally offer a tighter fit around the eyes.

Wearing protective eyewear can prevent 90% of sports-related injuries. Eyeglasses and contact lenses do not provide protection and can even place an athlete at an increased risk for such injuries. The American Academy of Ophthalmology has instituted a campaign for mandatory eyewear for children participating in school-related or community-sponsored athletic events. The Academy recommends that young athletes wear shatterproof goggles, constructed of 3 mm polycarbonate, that are fitted by an eye care professional.

In general, those individuals that are injured often wear inappropriate safety or ill-fitting eyewear for the task being undertaken, or do not wear protective eyewear at all times while undertaking the task. The finding that safety glasses may not provide adequate protection against small, off-center particles needs to be addressed, and the use of goggles promoted. According to OSHA, eye protection must, protect against the specific hazard(s) encountered in the workplace, be reasonably comfortable to wear, not restrict vision or movement, be durable and easy to clean and disinfect and not interfere with the function of other required personal protection equipment.

The reasons people give for not wearing safety goggles include, the safety goggles cause headaches, the eye protection is too hot to wear, the goggles are constantly dirty, the eye protection fogs over, the safety glasses never fit correctly, the goggles do not fit over prescription eyeglasses, the goggles lack style or comfort, and cause distortion and limit the field of vision.

Information relevant to attempts to address these problems can be found in U.S. Pat. Nos. 5,966,746, 5,519,896, 6,357,053, 5,771,499 and 6,178,561. However, each of these references suffers from one or more of the following disadvantages: inability to use existing prescription glasses while wearing the goggles, excessive goggle weight, limitations on range of vision such as obstruction of peripheral vision, uncomfortable to wear because of pressure applied to the head by bands and straps and internal fogging of the lenses brought about by perspiration, and at times respiration, of the wearer.

The present invention attempts to use the geometry of the housing and its various surfaces such as the arcuate upper surface and the lower panels to minimize the refraction of the light rays as they transit through the housing. If both old art and the present invention were made from the same material (for example polycarbonate) with the same refractive index, then the housing geometry of the present invention will minimize the angle of incidence of the light to produce a goggle with improved visual characteristics and principally less distortion.

Therefore, it is an object of the present invention to provide an improvement in the structure of safety goggles which can obviate or substantially lessen the above-mentioned drawbacks.

SUMMARY OF THE INVENTION

The present invention is directed to goggles that satisfy the demand for maximizing wearing comfort through ergonomic construction, maximizing field of view, minimizing distortion and minimizing fogging. A goggle having features of the present invention comprises a transparent housing with an arcuate upper surface with a first end and a second end, a planar frontal surface, a centrally disposed nose bridge and a first and second lower panel disposed opposite the nose bridge. The first and second lower panel join the arcuate upper surface proximate the arcuate upper surface first end and second end while the housing is contoured to conform to the topography of the wearer's face. Vents are disposed adjacent the nose bridge and means for supporting the goggle on the head of the wearer.

The housing's transparent upper surface is curved, or arcuate in configuration, to minimize the refraction of light that occurs when the angle of incidence of the light deviates from normal. Reducing, or preferably eliminating, the refraction of light will produce clearer vision with less distortion. The goggle housing is configured to accommodate the glasses of a wearer and also preserve the ability of the wearer to see superiorly, laterally and inferiorly to increase the field of vision or view.

Because of the ergonomic design, the goggle is capable of accommodating a large range of facial topographies and can also accommodate a large variety of glasses without the goggle being excessively heavy or producing the sensation that the goggle is attempting to fall from the face of the wearer. The goggle of the present invention is scalable and can be produced in a variety of sizes. The radius of the arcuate upper surface can be adjusted during the manufacturing process to produce goggles for children and adults alike by varying the radius dimension associated with the arcuate upper surface and other critical dimensions.

The preferred embodiment has a housing with an arcuate upper surface, a substantially planar frontal surface, a centrally disposed nose bridge and two lower panels disposed opposite the nose bridge from each other and joining the arcuate upper surface at the ends of the arcuate upper surface. The housing is contoured to conform to the topography of the individual's face and utilizes vent means disposed adjacent the nose bridge to facilitate movement of air. The goggle has support arms that extend rearward toward the ears of the wearer, and means to support the goggle on the head of the wearer.

The arcuate upper surface, planar frontal surface, centrally disposed nose bridge and at least a portion of the two lower panels are comprised of a transparent material. The support arms and a portion of the lower panels, which are beyond the range of the peripheral vision of the wearer, may be opaque for aesthetic purposes. Compressible padding will be attached to the rim of the housing providing a comfortable and close fit to the face of the wearer. This goggle has a unique ergonomic design, fashionable, sleek and futuristic looking and is contoured to conform to the topography of the individual's face therefore requiring a minimum amount of tension with a head band to hold it in position on the head of the wearer. The sleek ergonomic design is light in weight and because it distributes a force across the entire edge of the goggle it significantly improves wearing comfort as compared to many prior art designs.

The design of the present invention enhances the optical characteristics over the existing art. Specifically, because of the arcuate upper surface and slanted lower panels the angle of incidence of the light rays passing through the housing to enter the eyes of the wearer is reduced as compared to existing art. Therefore, refraction of light passing through the housing is minimized because the angle of incidence is reduced as compared with existing art. The design allows a full temporal field of vision of as close to 180 degrees as possible. The arcuate upper surface and lower panels allow for an unrestricted superior and inferior field of vision because the housing is made from the same material such as clear plastic or shatterproof glass to name but a few of the materials possessing the appropriate properties.

Usually, goggles pinch the eyeglasses at the nose bridge area or at the temple arms. Goggles are typically made to accommodate eyeglasses by making them oversized. Oversizing adds to the weight and interferes with their cosmetic appearance and comfort, thus resulting in non-use and subsequent eye injuries. The present invention is uniquely designed to accommodate eyeglass frames and temple arms. This goggle's design positions the frontal surface far above, below, and to the front of the usual place of the nose bridge of the eyeglasses. Also, the support arms exhibit a wedge shaped space to accommodate the temple arms of the eyeglasses. In addition, the housing is configured to be used with a virtual reality visor. Thus, this design provides the optimal amount of space with the minimal amount of weight.

The goggle design allows it to be a universal fit and to accommodate most sizes of eyeglass frames. The nose bridge is designed to fit a wide range of noses and the bridge portion is placed in a very close anatomical relationship to the nostrils of the wearer. By placing the vents in the padding of the nose bridge portion, the close proximity of the vents to the nose allows the nose to draw air out of the vents during inhalation. Consequently, the nose will act as a natural suctioning device, forcing the air to circulate within the goggle with every breath of the wearer. The air circulation will reduce fogging of the goggle. Breathing with the nose drawing air in from its surrounding facial area will force air out of the goggle. Air will be drawn into the goggle from holes placed in the temple arms.

Because this goggle conforms to the face of the wearer and has support means that consist of rearward extension of the arcuate upper surface and the lower panels, the head-encompassing member maintains its position against the face with the least amount of pressure. The head-encompassing member and the padding facilitate the formation of a seal between the housing and the face of the user that limits the entry of debris or chemicals to the eye.

These and other features, aspects, and advantages of the present invention will become better understood with reference to the following description, appended claims and accompanying drawings.

BRIEF DESCRIPTION OF THE SEVERAL VIEWS OF THE DRAWING

FIG. 4 is a plan view of a protective goggle constructed in accordance with the preferred embodiment of the present invention, illustrating the placement of a wearer's eye glasses in a use position;

FIG. 5 is a rear elevation view of a protective goggle constructed in accordance with the preferred embodiment of the present invention, illustrating the placement of a wearer's eye glasses in a use position;

DETAILED DESCRIPTION OF THE INVENTION

While this invention is susceptible of embodiments in many different forms, this specification and the accompanying drawings disclose only preferred embodiments of the invention. The invention is not intended to be limited to the embodiments so described, and the scope of the invention will be pointed out in the appended claims.

Figure 3:
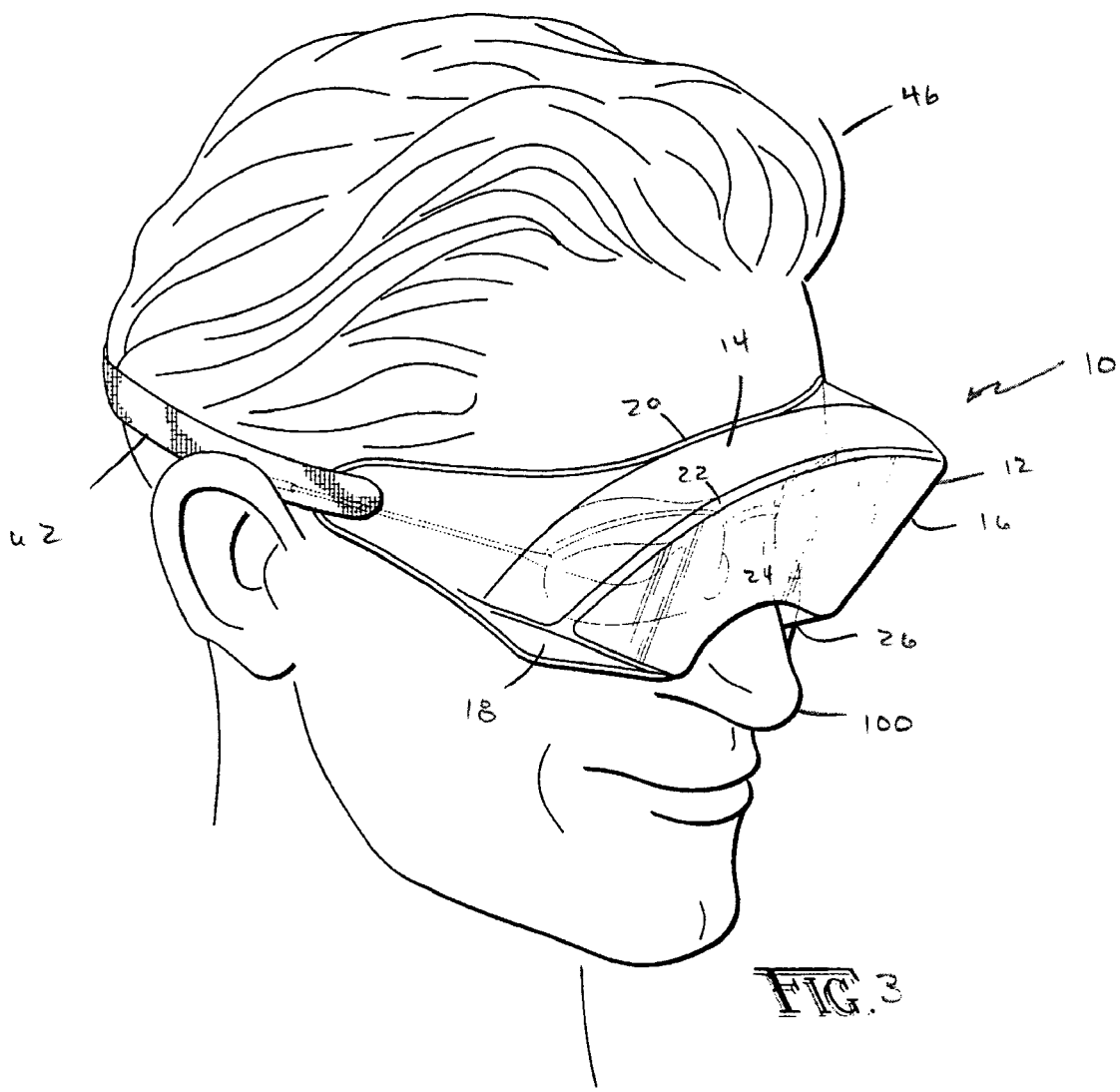
FIG. 3 is a perspective view of a protective goggle constructed in accordance with the preferred embodiment of the present invention, illustrating the goggle in a use position on the face of a wearer.

The preferred embodiment and best mode of the present invention is shown in FIGS. 3 through 5. At FIG. 3, a protective goggle constructed in accordance with the teachings of the present invention is shown generally at 10. The present invention is principally directed to use by individuals engaged in sporting events and industrial work settings that may potentially be harmful to the eyes if they are improperly protected. Examples of sporting events for which these goggles would be appropriate are racquetball, skiing, basketball and baseball. All of which have either a ball moving at a high rate of speed or the potential for eye injury through high energy impact with other individuals. In industrial settings, for example, flying debris presents a persistent threat to the safety of the eye and must be guarded against.

As shown in FIGS. 3 through 5 the protective goggle 10 includes a housing 12 with an arcuate upper surface 14 with a first end 16 and a second end 18, a posterior edge 20 and an anterior edge 22, a substantially planar frontal surface 24, a centrally disposed nose bridge 32 and a first and second lower panel 28, 30 disposed opposite the nose bridge 32. The first and second lower panels include an anterior portion 34, 36 wherein the first and second ends of the substantially planar frontal surface intersect the first and second lower panels. The first and second lower panels 28, 30 include a lateral portion 38, 40 wherein the first and second ends of the arcuate upper surface intersect the lateral portion of the first and second lower panels 28, 30. The first and second lower panels 28, 30 join the arcuate upper surface 14 at the first end 16 and second end 18.

As best seen in FIG. 5, the lower panels 28, 30 also include an edge contoured to conform to the topography of the face of the wearer 42, 44. The housing 12 is contoured to conform to the topography of the wearer's face 46 along posterior edge 20 and in the preferred embodiment will utilize foam padding (not shown) to improve wearing comfort.

Strategically placed vents 48, 50 adjacent the nose bridge 32 allow the movement of moisture laden air out of the housing thereby minimizing fogging. The housing 12 support arms 52, 54 extend rearwardly towards the user's ears approximately 3 to 5 inches from the substantially planar frontal surface 24. As seen in FIG. 4, the support arms 52, 54 are sufficiently robust in their wedge shaped dimension in order to accommodate the passage of the arms 56, 58 of a pair of glasses 60. At the same time, the support arm 52, 54 dimensions are minimized to increase wearing comfort. The goggles 10, as best seen in FIGS. 3 and 7, also utilize a strap 62 or other appropriate securing device to support the goggle 10 on the head 64 of the wearer.

The housing 12 is preferably formed of a shatter resistant material nominally 3 mm in thickness; however, other thicknesses may be employed based upon the need of the individual consumer. Examples of the shatter resistant materials include, but are not limited to plastic and glass. In the preferred embodiment of the invention, the housing 12 is an integrally molded article preferably formed as a single piece, however, a construction utilizing support arms separately snapped, glued or riveted to the main portion of the housing may also be utilized. The housing 12 can be produced using standard injection molding techniques.

Figure 6:
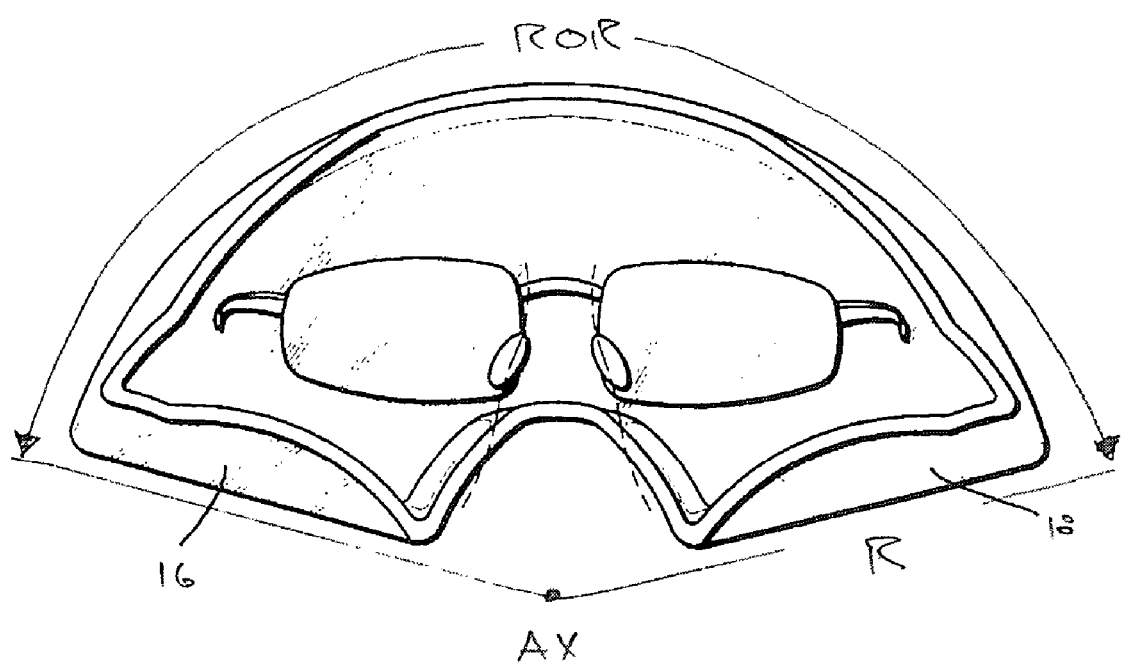
FIG. 6 is a rear elevation view of the protective goggle constructed in accordance with the preferred embodiment of the present invention illustrating the radius "R" and range of rotation "ROR" of the arc.
Figure 7:
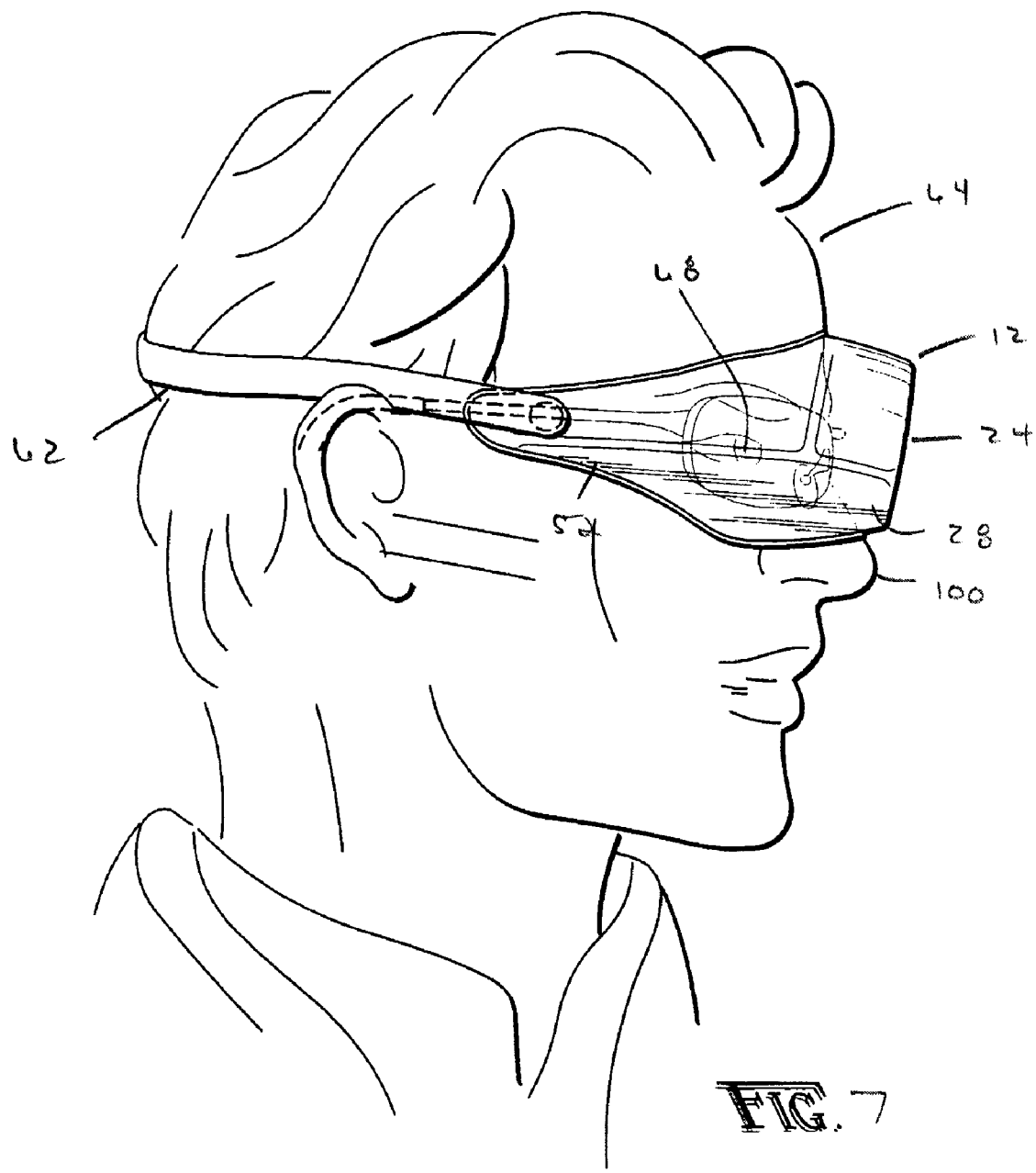
FIG. 7 is a side elevation view of a protective goggle constructed in accordance with the preferred embodiment of the present invention, illustrating the goggle in a use position on the face of a wearer.

As shown in FIG. 7, the preferred embodiment of the housing 12 is sufficiently offset from the face 46 of the wearer to accommodate a wide range of eye glasses 60. The housing 12 is configured to position the planar front surface 20 approximately 3 cm from the surface of the wearer's pupil 68. A distance of 3 cm between the pupil 68 of the wearer's eyes and the planar frontal surface 24 is approximately one entire centimeter more than most other protective goggles provide such as with a goggle manufactured by AO Safety™. The additional centimeter of distance provides for increased overall wearing comfort because the housing 12 is sufficiently spaced from the wearer's glasses 60 and will avoid the application of pressure to the face 46 of the wearer. As shown in FIGS. 6 and 7 the housing is sufficiently spacious to accommodate a pair of glasses without interference between the lenses 70 and the frame 72 and the housing interior 72.

The configuration of the arcuate upper surface 14, as best seen in FIG. 6, is defined by an arc, or a range of rotation "ROR," with an axis of rotation extending perpendicularly out of the page at a point "AX" coincident with the tip 100 of the nose of the wearer. The range of rotation extends between the first end 16 and the second end 18. The distance "R" is between 2.5 and 4 inches depending upon the preferred size of the goggle, and a range of rotation "ROR" of between 120 and 180 degrees from first end 16 to second end 18 of the arcuate upper surface. A preferred embodiment would utilize a range of rotation "ROR" from between 130 to 150 degrees between the first end 16 and the second end 18 of the arcuate upper surface. The dimension "R" and the range of rotation "ROR" are determined by the facial dimensions of the wearer. For example, a child may require a smaller goggle with a radius "R" of approximately 2.5 inches while an adult male with larger facial features may require a goggle with a radius "R" of up to 4 inches.

As best shown in FIG. 5, the housing 12 also utilizes strategically positioned vents 48, 50 positioned adjacent the nose bridge 32. The vents 48, 50 are critical for minimizing the condensation of moisture on the interior 72 of the housing 12. If moisture condenses on the interior 72 of the housing it presents a potentially dangerous situation for the wearer as the clarity of view may be substantially diminished. Particularly when playing sports and when exposed to dangerous industrial environments it is critical to minimize the formation of condensation on the interior 72 of the housing 12. The vents 48, 50 are positioned adjacent the nose bridge 32 and in proximity to the nose of the wearer to facilitate removal of excess moisture by relying upon a minor drop in pressure in proximity to the nose bridge when the wearer inhales through the nose. The de minimis localized drop in pressure produces a minor outflow of the air contained within the housing interior 72 thereby removing the high moisture content air contained therein. The ambient air pressure and the interior 72 air pressure are quickly equalized with lesser moisture content air entering through the support arms 52, 54.

Figure 1:
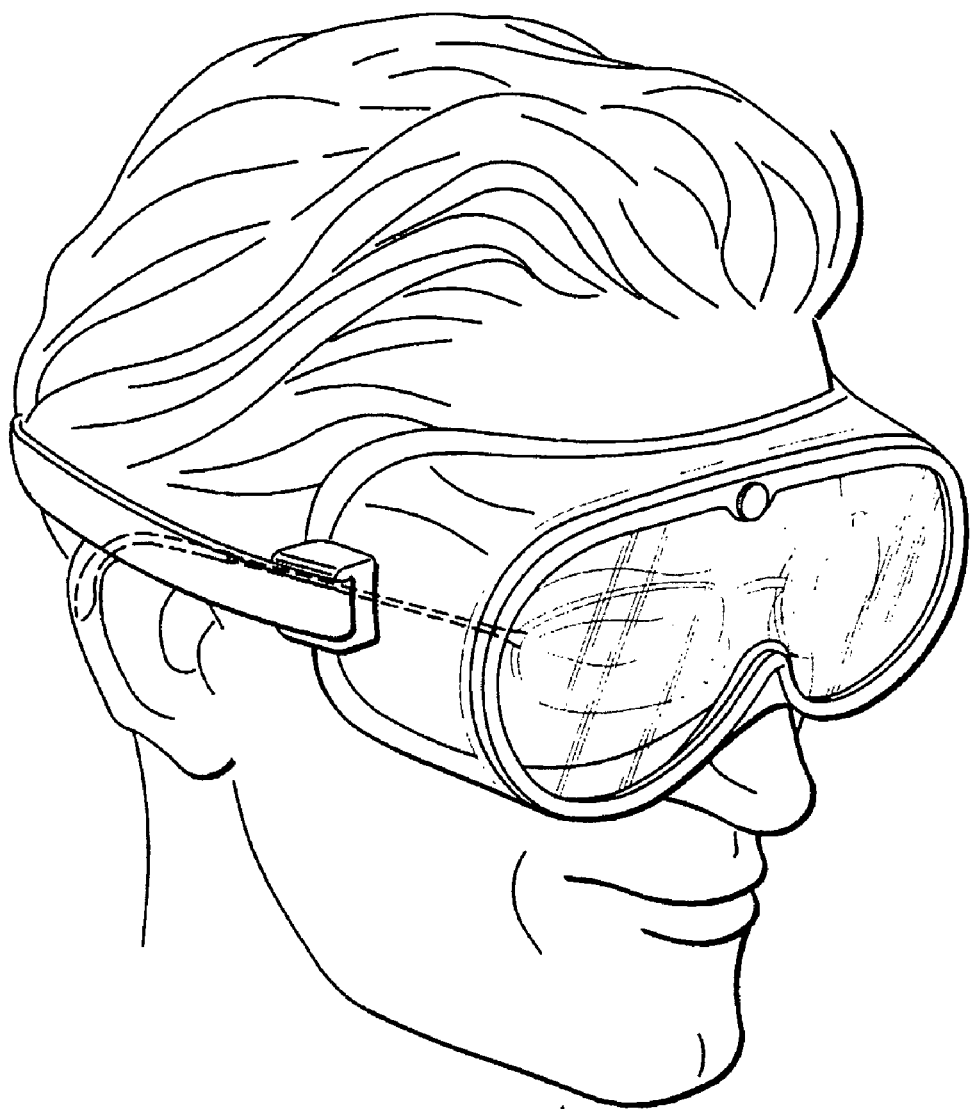
FIG. 1 is a perspective view of a prior art goggle illustrating the goggle in a use position on the face of a wearer.
Figure 2:
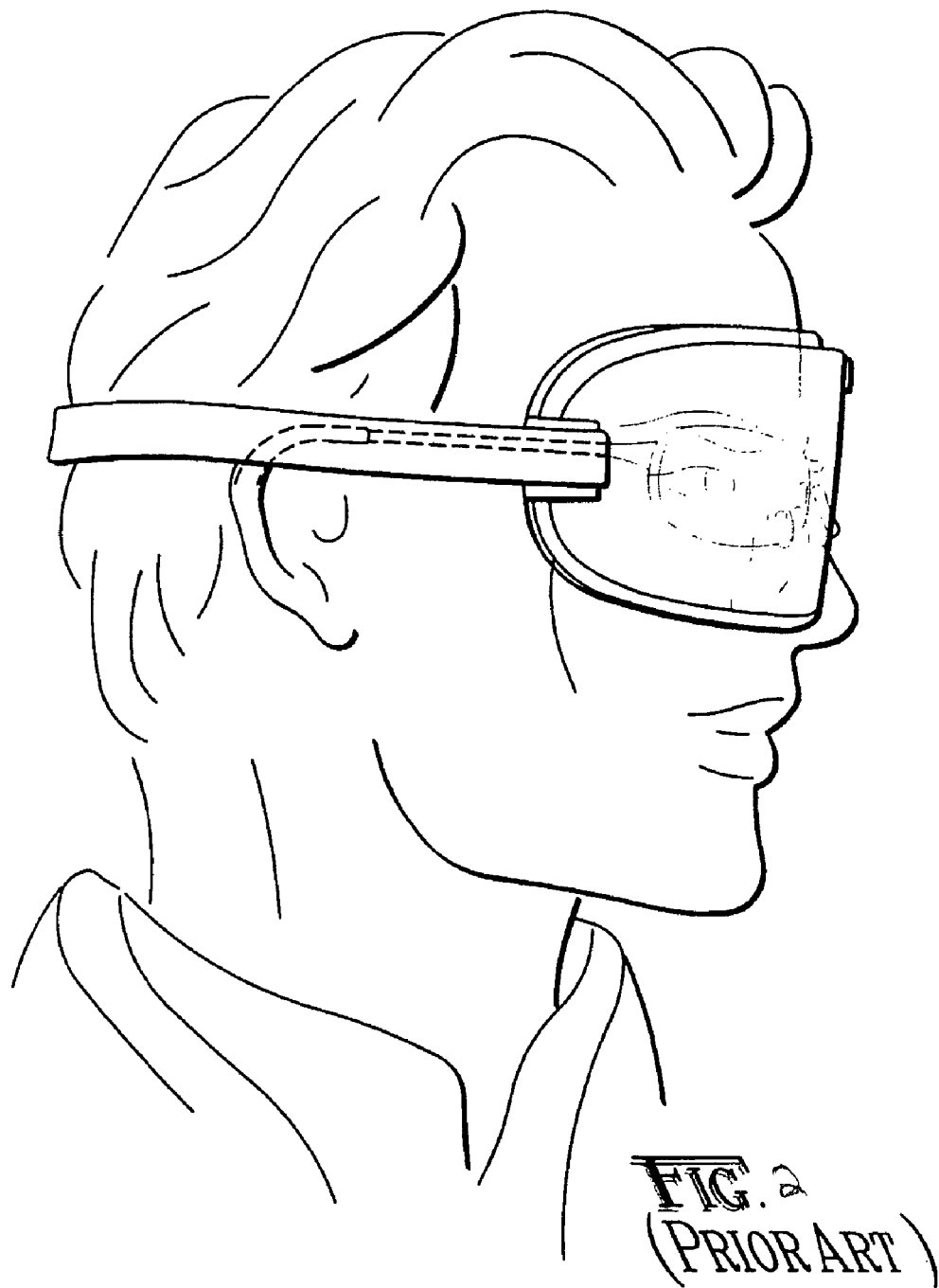
FIG. 2 is a side elevation view of a prior art goggle illustrating the goggle in a use position on the face of a wearer.
Figure 8:
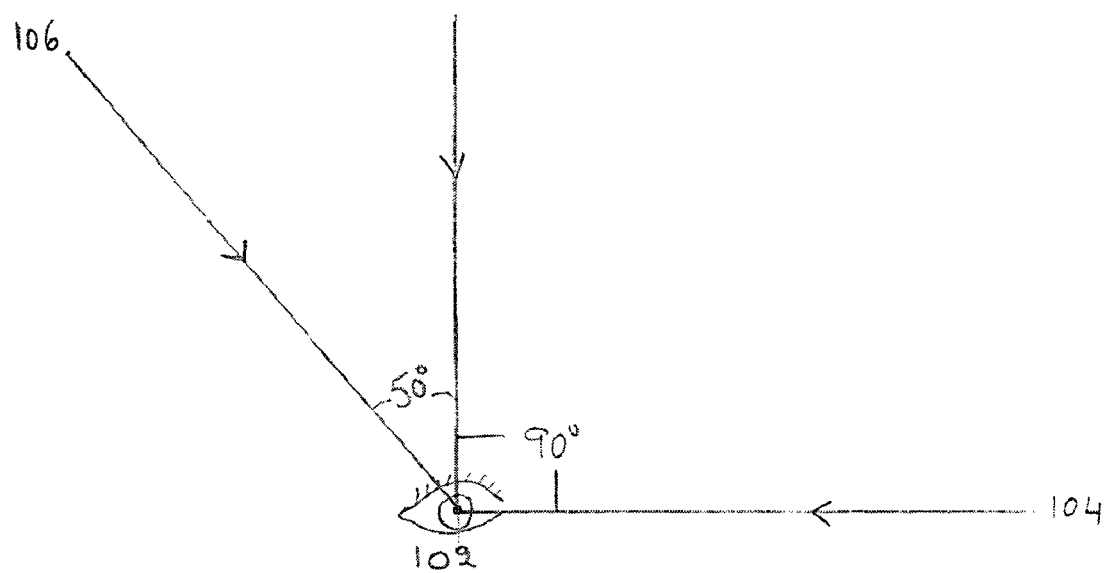
FIG. 8 is a diagram depicting a frontal view of the visual field of a human eye.
Figure 9:
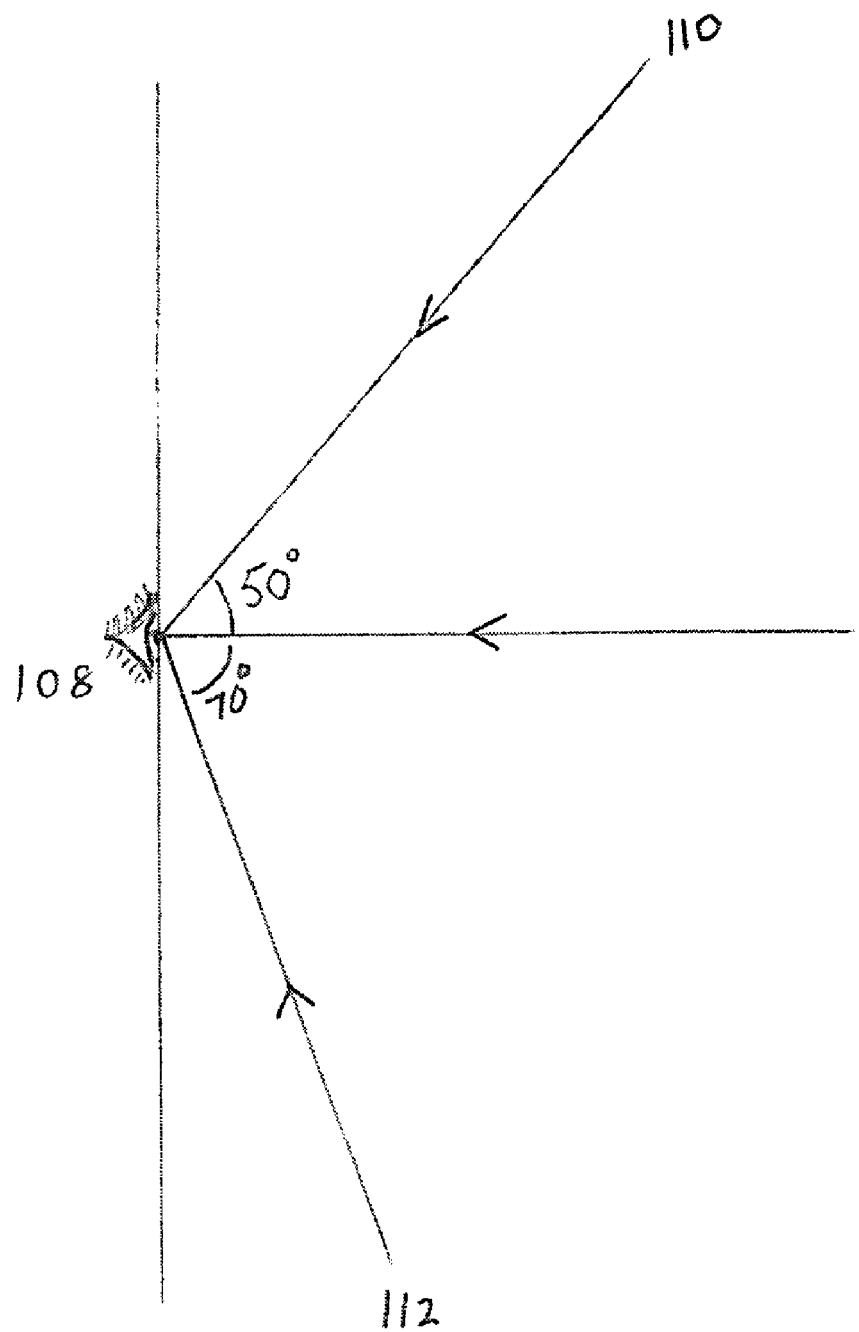
FIG. 9 is a diagram depicting a side view of the extremes of the visual field of a human eye.

As shown in FIG. 8. a healthy human eye 102 has a temporal field of view 104 of approximately 90 degrees and a nasal field of view 106 of approximately 50 degrees. With many prior art goggles the temporal field of view 104 can be obstructed by the structure of the goggle such as is seen in FIG. 1. The present invention seeks to avoid any obstruction of the temporal field of view. The goggle 10 upper surface 14, front panel 20 and the first and second lower panels 28, 30 are configured to minimize the obstructions to the users field of view. A full field of view is critically important in sporting events and industrial settings where sensory input on fast moving objects and dangerous conditions is vital to personal safety. As seen in FIG. 9, a healthy human eye 108 has a superior field of view 110 of approximately 50 degrees and an inferior field of view 112 of approximately 70 degrees.

Figure 10:
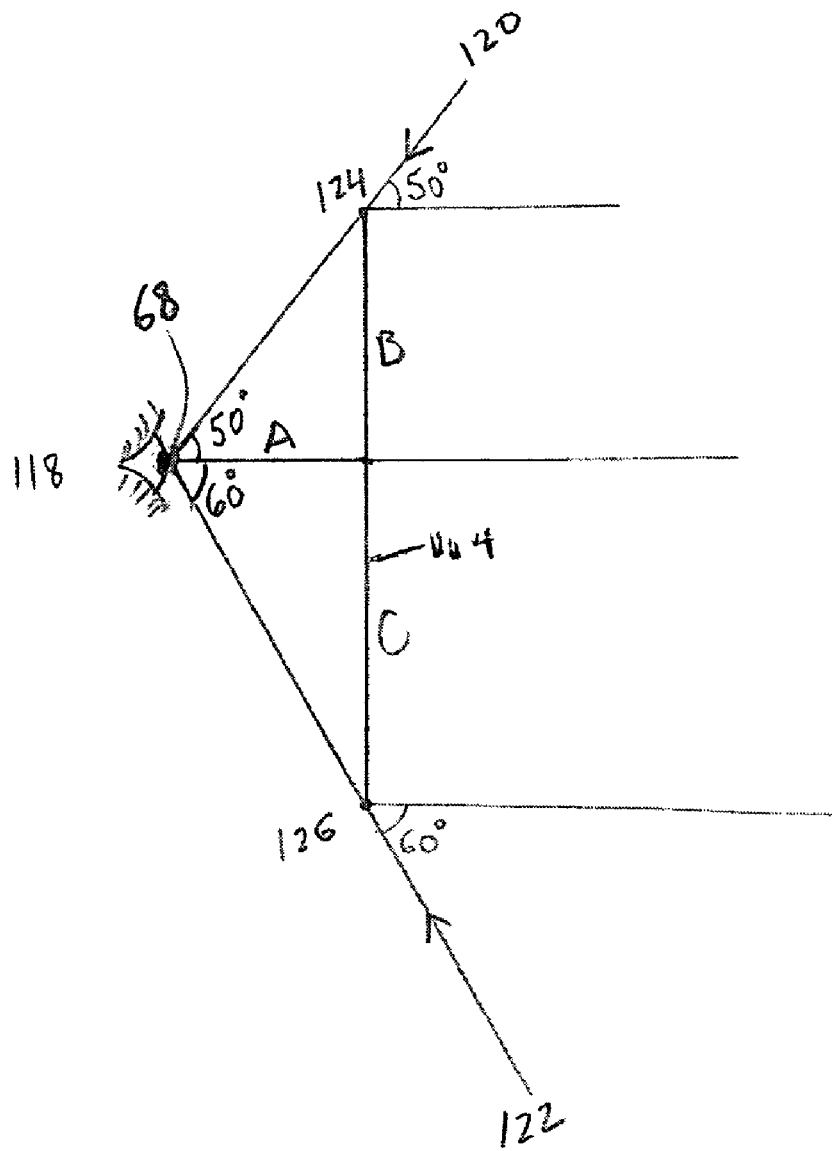
FIG. 10 is a diagram depicting light rays coming from the superior and inferior visual field and intersecting with the frontal surface of a prior art goggle placed at 2 cm distance from the eye with the maximum angle of incidence being 50 degrees and 60 degrees respectively.
Figure 11:
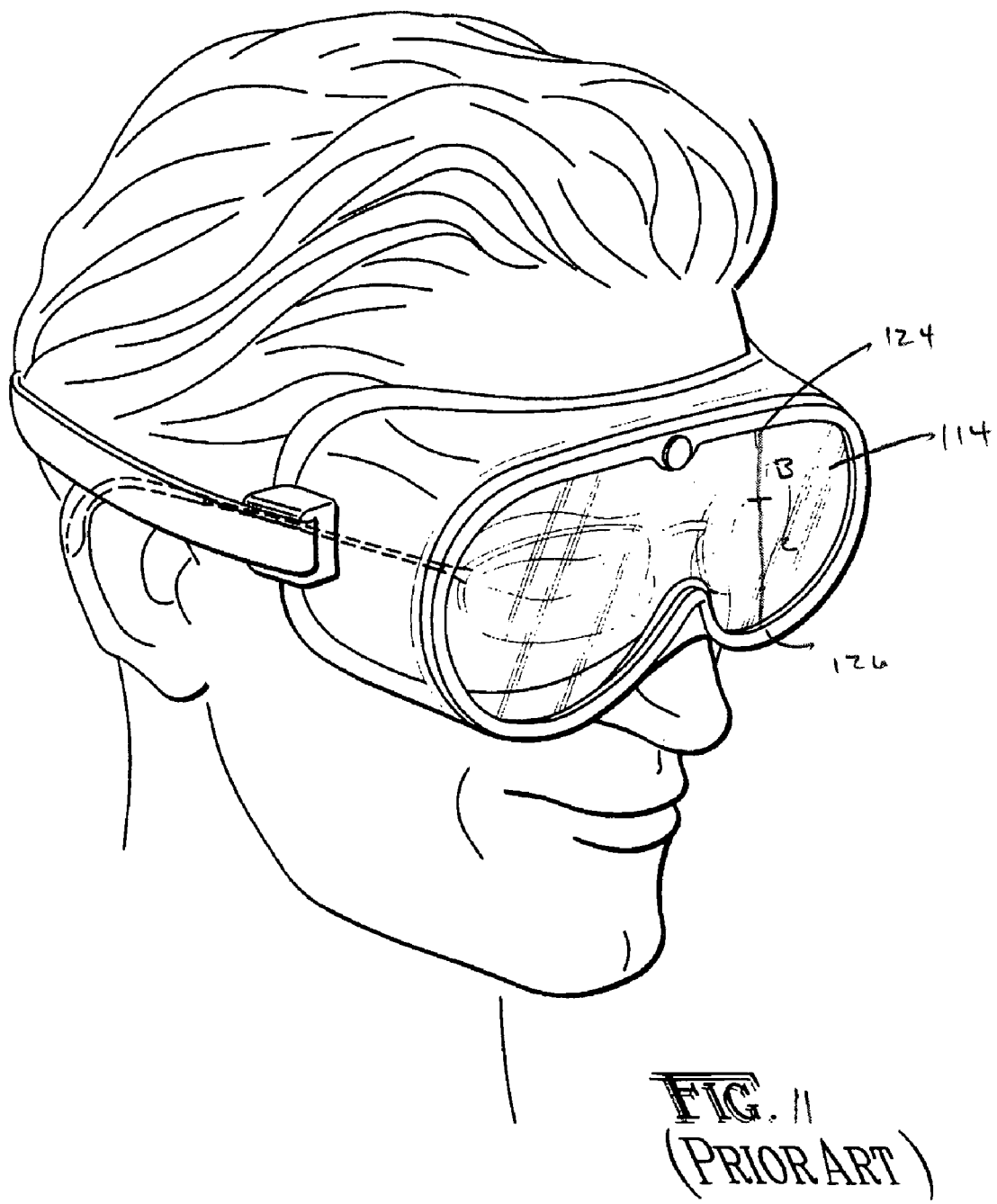
FIG. 11 is a perspective view of a prior art goggle illustrating the goggle in a use position on the face of a wearer with a cross-hair locating the center of vision of the wearer's eye and identifying the available inferior and superior field of view through the front panel.

FIG. 10 presents a diagrammatic representation of a prior art goggle frontal surface 114 positioned at a distance "A" of approximately two centimeters from the pupil 68 of the wearer's eye 118. The diagram also depicts the superior 120 and inferior 122 fields of view and the intersection points 124, 126 of the prior art goggle front surface with the upper and lower surfaces. As seen in FIGS. 10 and 11, some prior art goggles utilized a frontal surface 114 that extended no more than a distance B, about 2.5 centimeters above the centerline of the pupil 68 to the intersection 124 with the upper surface thereby limiting the superior field of view 120. In addition, many old art goggles utilized a distance C of about 3.5 centimeters below the pupil thereby limiting the inferior field of view 122. The superior and inferior fields of view were limited in that the upper and lower surfaces of the prior art goggles are opaque.

The angle of incidence for light traveling from the farthest edge of a typical prior art frontal surface as represented in FIGS. 10 and 11 is 60 degrees for the lower intersection 126 and 50 degrees for the upper intersection 124. The amount of refraction of the light is dependent upon the angle at which light strikes the housing 12 material. The greater the angle of incidence, the greater the angle of refraction (not shown). Goggles with a greater angle of refraction present a less desirable goggle for sporting and industrial purposes because as the angle of refraction increases so too does the optical illusion as to the perceived position of an object. Goggles that minimize the angle of refraction over the entire field of view are superior to those with greater angles of refraction over the entire range of view because they cause less distortion of the incoming light rays.

Figure 12:
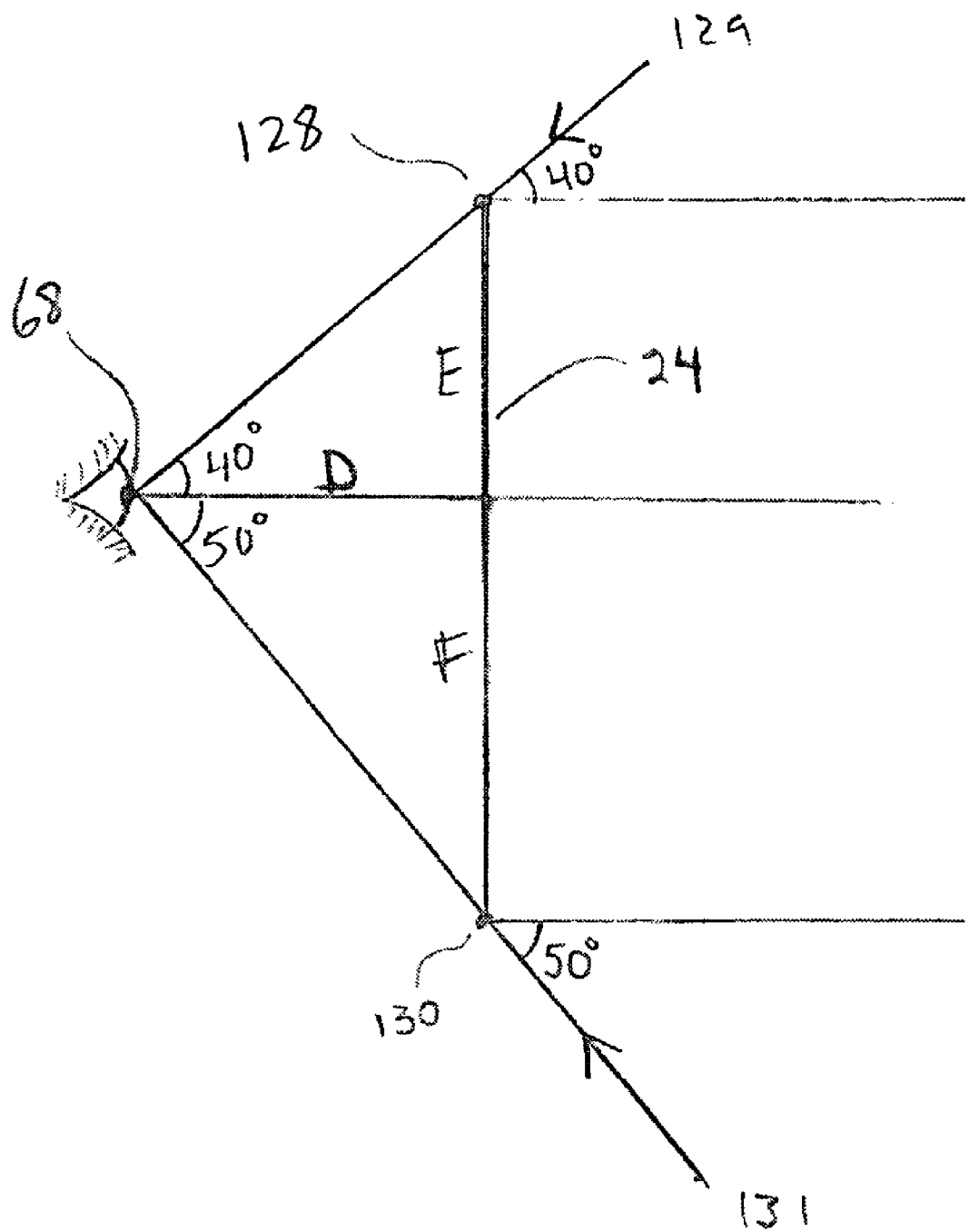
FIG. 12 is a diagram depicting light rays coming within the field of view of a human eye, the light rays intersecting with the extreme upper and lower edges of the frontal surface of an embodiment of the present invention placed at 3 cm distance from the eye with the maximum angle of incidence being 40 degrees and 50 degrees respectively.
Figure 13:
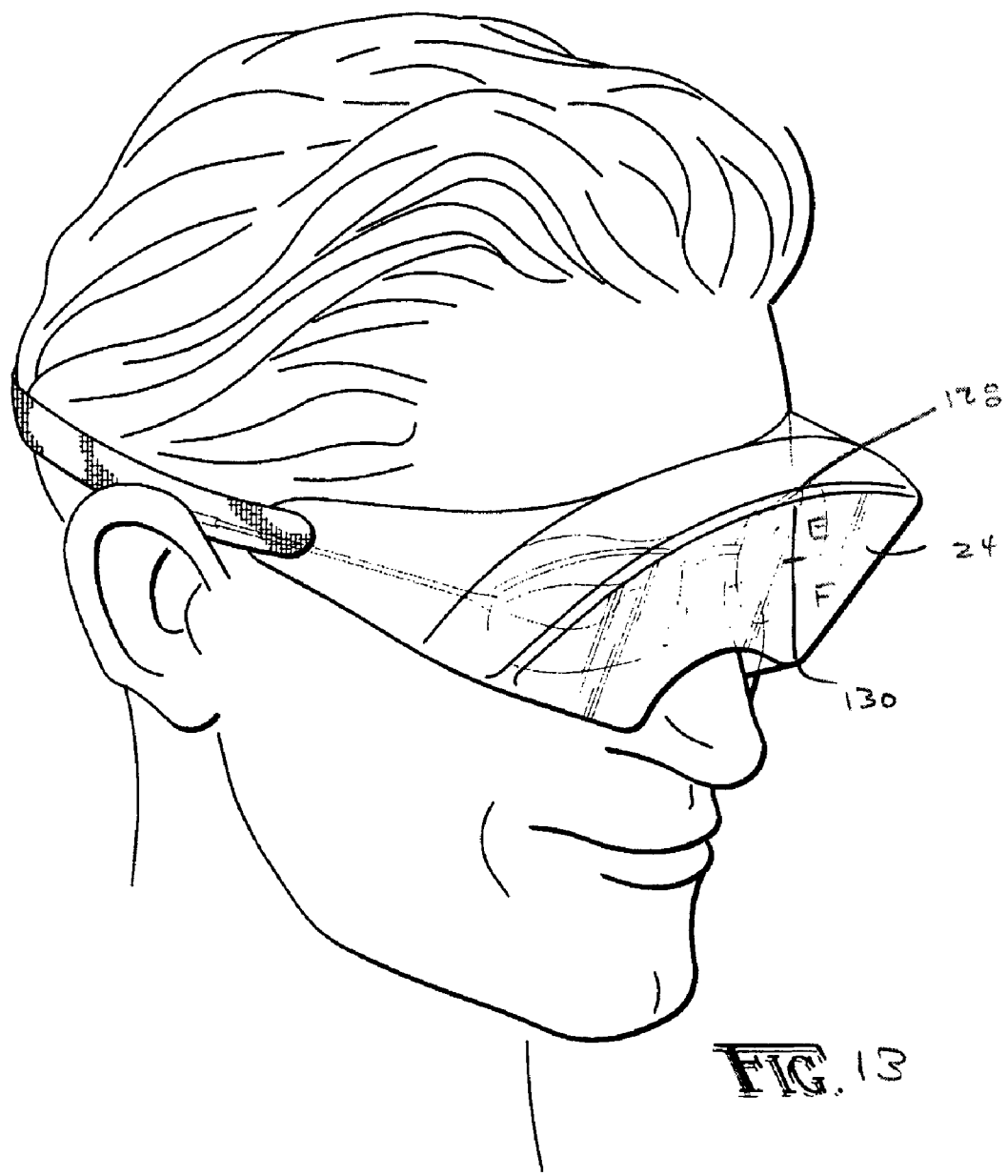
FIG. 13 is a perspective view of a protective goggle constructed in accordance with the preferred embodiment of the present invention, illustrating the goggle in a use position on the face of a wearer with a cross-hair locating the center of vision of the wearer's eye and identifying the available inferior and superior field of view through the front panel.

FIG. 12 shows a substantially planar frontal surface 24 of the present invention positioned at a distance D of approximately three centimeters from the pupil 68 of the wearer. The diagram also depicts the superior 129 and inferior 131 fields of view and respectively the intersection 128 of the frontal surface 24 with the arcuate upper surface 14 and the intersection 130 of the frontal surface with the lower panels 28, 30. As seen in FIGS. 12 and 13, the present invention utilizes a frontal surface 24 that extends no more than a distance E, about 2.5 centimeters above the center line of the pupil 68 to the intersection 128 with the upper surface. In addition, the new invention utilizes a viewing range of about 3.5 centimeters from the center line of the pupil 68 to the lower intersection 130 of the frontal surface with the lower panels 28, 30. The angle of incidence for light traveling from the farthest edge of the present invention as represented in FIGS. 12 and 13, is 50 degrees for the lower intersection 130 and 40 degrees for the upper intersection 128.

Figure 14:
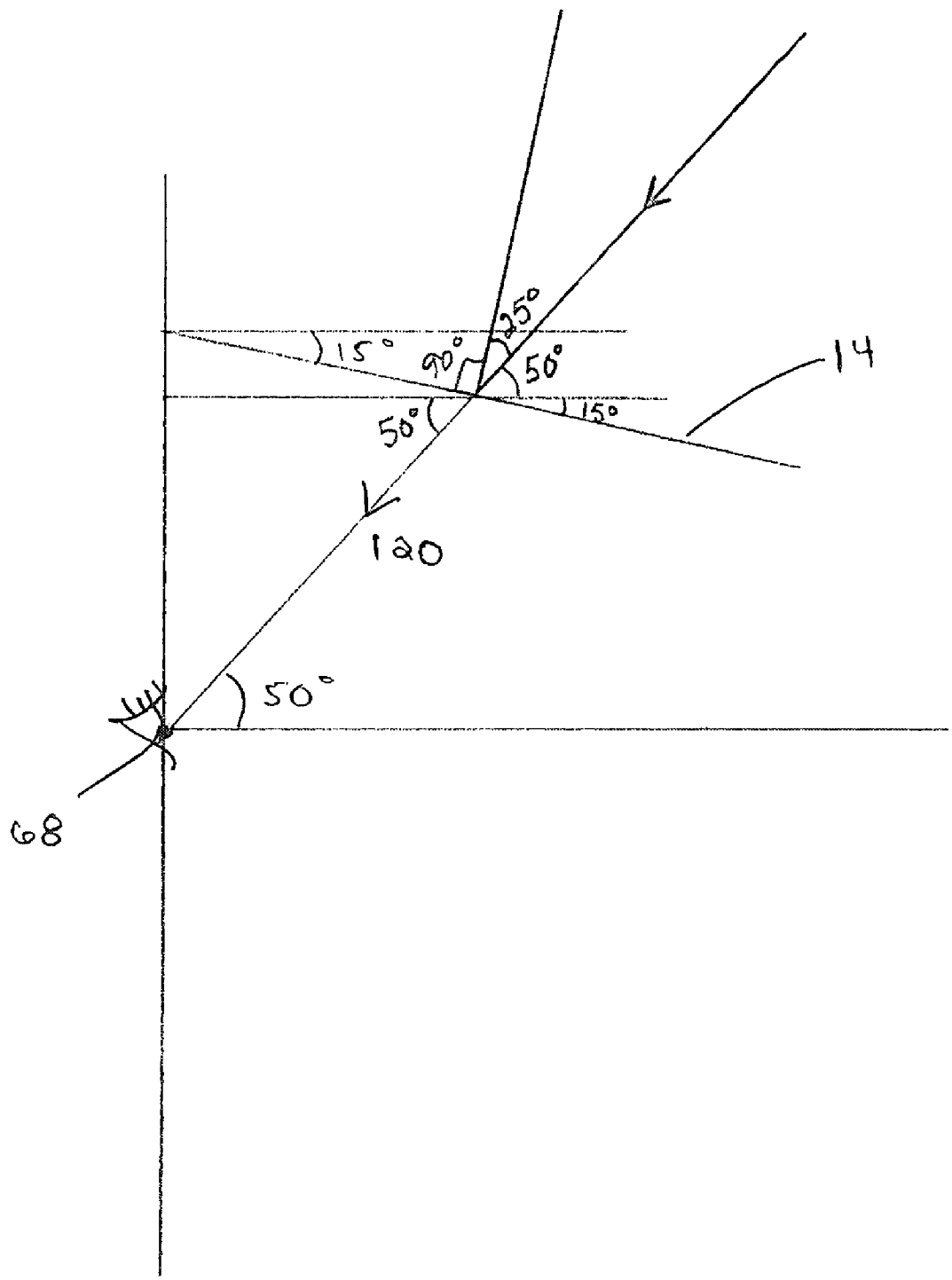
FIG. 14 is a diagram depicting a side view of light rays coming from a 50 degree angle of the field of vision superiorly intersecting with the upper surface of an embodiment of the present invention, with calculation of the angle of incidence being 25 degrees.

FIG. 14 shows an exemplary placement of the arcuate upper surface 14 declining from the horizontal at 15 degrees and an exemplary light ray 120 intesecting from a 50 degree angle of the field of vision superiorly. The angle of incidence of the intersecting light ray 120 is calculated at 25 degrees where it intersects with the arcuate upper surface 14, which is 25 degrees less than the angle of incidence of the same light ray 120 for old art as shown in FIG. 10. Based upon a placement of the frontal surface 24 (not shown) a distance of approximately 3 centimeters from the pupil 68 of the wearer, the angle of the upper surface 14 to the horizontal can obviously be varied as necessary to suit particular needs; nonetheless, a preferred embodiment would establish the arcuate upper surface 14 declining at an angle of 15 degrees from the horizontal to produce a smaller angle of incidence of the light and likewise a smaller angle of refraction (not shown), relative to the pupil of the wearer, thereby reducing distortion.

Figure 15:
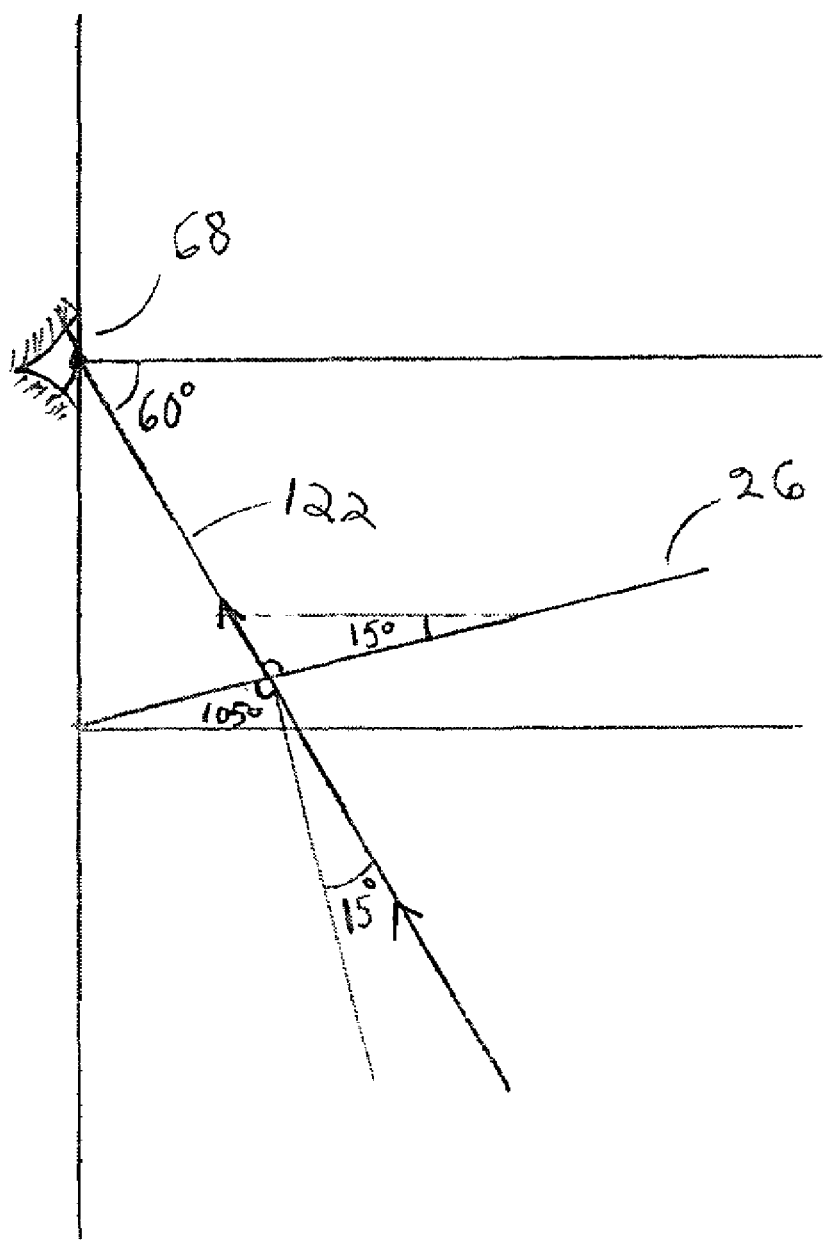
FIG. 15 is a diagram depicting a side view of a light ray coming from a 60 degree angle of vision inferiorly intersecting with a lower panel of an embodiment of the present invention with calculation of the angle of incidence being 15 degrees.

FIG. 15 shows an exemplary placement of the lower panel 26 at an angle 15 degrees from horizontal, and an exemplary light ray 122 intersecting from a 60 degree angle of the field of vision inferiorly. The angle of light ray 122 where it intersects with the lower panel 26 is calculated to be 15 degrees based upon a placement of the frontal surface 24 (not shown) a distance of approximately 3 centimeters from the pupil 68 of the wearer, which is 45 degrees less than the angle of incidence of the same light ray for old art as shown in FIG. 10. The angle of the lower panel 26 to the horizontal can obviously be varied as necessary to suit particular needs; nonetheless, a preferred embodiment would establish the lower panel 26 declining at an angle 15 degrees from the horizontal, to produce a smaller angle of incidence of the light and likewise a smaller angle of refraction (not shown), relative to the pupil of the wearer, thereby reducing distortion.

Although the present invention has been described in considerable detail with reference to certain preferred versions thereof, other versions are possible. Therefore, the spirit and scope of the appended claims should not be limited to the description of the preferred versions contained herein.

What is claimed is:

1. A goggle for applications requiring protection of the eyes of a wearer, the goggles comprising:
    a housing wit an arcuate upper surface with a first end and a second end;
    a substantially planar frontal surface;
    a centrally disposed nose bridge;
    a first and second lower panel disposed opposite the nose bridge, an edge of the first and second lower panel connecting with the arcuate upper surface first and second end;
    goggle support means for securing the goggle to the head of the wearer; and vent means disposed adjacent the nose bridge; and wherein the arcuate upper surface, substantially planar frontal surface and at least an anterior portion of the first and second lower panels are comprised of a transparent material.

2. A goggle for applications requiring protection of the eyes of a wearer, the goggles comprising:
   a housing with an arcuate upper surface with a first end and a second end;
   a substantially planar frontal surface;
   a centrally disposed nose bridge;
   a first and second lower panel disposed opposite the nose bridge, an edge of the first and second lower panel connecting with the arcuate upper surface first and second end;
   goggle support means for securing the goggle to the head of the wearer; and
   vent means disposed adjacent the nose bridge; and
   wherein the arcuate upper surface is defined by an arc with an axis of rotation extending perpendicular to the tip of the nose of a wearer with a radius of between about 2.5 to 4 inches and a range of rotation extending between about 120 degrees and 180 degrees from the arcuate upper surface first end to the arcuate upper surface second end.

3. The goggle according to claim 2, wherein the range of rotation extends between about 130 degrees and 150 degrees.

4. A goggle for applications requiring protection of the eyes of a wearer, the goggle comprising:
   a housing comprising;
   a substantially planar frontal surface;
   an arcuate upper surface with a first end and a second end, the arcuate upper surface further comprising a posterior edge and an anterior edge, the posterior edge contoured to conform to the topography of the face of the wearer, the anterior edge of the arcuate upper surface intersecting with the substantially planar frontal surface;
   a nose bridge centrally disposed between the first and second end of the planar frontal surface;
   a first and second lower panel, the first lower panel disposed opposite the nose bridge from the second lower panel, the first and second lower panels further comprising an anterior portion, a lateral portion and an edge contoured to conform to the topography of the wearer's face;
   support arms extending rearwardly from the arcuate upper surface first and second ends toward the ears of the wearer; and
   vents disposed adjacent the nose bridge; and
   wherein the first and second ends of the arcuate upper surface join the lateral portions of the first and second lower panels.

5. A goggle for applications requiring protection of the eyes of a wearer, the goggle comprising:
   a housing comprising:
   a substantially planar frontal surface;
   an arcuate upper surface with a first end and a second end, the arcuate upper surface further comprising a posterior edge and an anterior edge, the posterior edge contoured to conform to the topography of the face of the wearer, the anterior edge of the arcuate upper surface intersecting with the substantially planar frontal surface;
   a nose bridge centrally disposed between the first and second end of the planar frontal surface;
   a first and second lower panel, the first lower panel disposed opposite the nose bridge from the second lower panel, the first and second lower panels further comprising an anterior portion, a lateral portion and an edge contoured to conform to the topography of the wearer's face;
   support arms extending rearwardly from the arcuate upper surface first and second ends toward the ears of the wearer; and
   vents disposed adjacent the nose bridge; and
   wherein the arcuate upper surface, the substantially planar frontal surface and at least a portion of the first and second lower panels is comprised of a transparent material.

6. A goggle for applications requiring protection of the eyes of a wearer, the goggle comprising:
   a housing comprising;
   a substantially planar frontal surface;
   an arcuate upper surface with a first end and a second end, the arcuate upper surface further comprising a posterior edge and an anterior edge, the posterior edge contoured to conform to the topography of the face of the wearer, the anterior edge of the arcuate upper surface intersecting with the substantially planar frontal surface;
   a nose bridge centrally disposed between the first and second end of the planar frontal surface;
   a first and second lower panel, the first lower panel disposed opposite the nose bridge from the second lower panel, the first and second lower panels further comprising an anterior portion, a lateral portion and an edge contoured to conform to the topography of the wearer's face;
   support arms extending rearwardly from the arcuate upper surface first and second ends toward the ears of the wearer; and
   vents disposed adjacent the nose bridge; and
   wherein the arcuate upper surface is defined by an arc with an axis of rotation extending perpendicular to the tip of the nose of a wearer with a radius of between about 2.5 to 4 inches and a range of rotation extending between about 120 degrees and 180 degrees from the arcuate upper surface first end to the arcuate upper surface second end.

7. A method for making a goggle for protecting the eyes, the method comprising the steps of:
   providing a housing with an arcuate upper surface with a first end and a second end, a planar frontal surface, a centrally disposed nose bridge, a first and second lower panel disposed opposite the nose bridge, an edge of the first and second lower panel connecting with the arcuate upper surface first and second end, the housing contoured to conform to the topography of the wearer's face;
   providing means for supporting the goggle on the head of the wearer; and providing vent means disposed adjacent the nose bridge; and
   wherein the arcuate upper surface, substantially planar frontal surface and at least an anterior portion of the first and second lower panels are comprised of a transparent material.

8. A method for making a goggle for protecting the eyes, the method comprising the steps of:
   providing a housing with an arcuate upper surface with a first end and a second end, a planar frontal surface, a centrally disposed nose bridge, a first and second lower panel disposed opposite the nose bridge, an edge of the first and second lower panel connecting with the arcuate upper surface first and second end, the housing contoured to conform to the topography of the wearer's face;

providing means for supporting the goggle on the head of the wearer; and providing vent means disposed adjacent the nose bridge; and wherein the arcuate upper surface is defined by an arc with an axis of rotation extending perpendicular to the tip of the nose of a wearer with a radius of between about 2.5 to 4 inches and a range of rotation extending between about 120 degrees and 180 degrees from the arcuate upper surface first end to the arcuate upper surface second end.

9. The method according to claim 8, wherein the range of rotation extends between about 130 degrees and 150 degrees.

* * * * *